United States Patent [19]

Kamstrup-Larsen

[11] Patent Number: 4,840,692
[45] Date of Patent: Jun. 20, 1989

[54] METHOD FOR PRODUCING AN ABSORPTION BODY, NOTABLY FOR USE IN CASES OF URINARY INCONTINENCE IN WOMEN

[75] Inventor: Jorgen Kamstrup-Larsen, Allerod, Denmark

[73] Assignee: Coloplast A/S, Denmark

[21] Appl. No.: 122,215

[22] Filed: Nov. 18, 1987

Related U.S. Application Data

[63] Continuation of Ser. No. 855,640, Apr. 16, 1986, abandoned.

[30] Foreign Application Priority Data

Aug. 21, 1984 [DK] Denmark .................................. 3988
Aug. 21, 1985 [WO] PCT Int'l Appl. .................... PCT/DK85/00081

[51] Int. Cl.$^4$ .............................................. B32B 31/18
[52] U.S. Cl. .................................... 156/252; 156/253; 156/257; 604/368
[58] Field of Search .................... 156/252, 253, 62.6, 156/62.8, 279, 283, 308.2, 308.4, 308.6, 320; 604/368, 378, 379, 380, 385.1

[56] References Cited

U.S. PATENT DOCUMENTS

| 3,343,543 | 9/1967 | Glassman | 604/368 |
| 3,403,681 | 10/1968 | Hoey et al. | 156/253 |
| 3,441,023 | 4/1969 | Rijssenbeek | 604/368 |
| 3,620,894 | 11/1971 | Oates | 156/253 |
| 3,670,731 | 6/1972 | Harmon | 604/368 |
| 3,746,592 | 7/1973 | Nystrand et al. | 156/253 |
| 3,749,627 | 7/1973 | Jones | 156/252 |
| 4,082,886 | 4/1978 | Butterworth et al. | 156/62.8 |
| 4,333,464 | 6/1982 | Nakano | 604/368 |
| 4,381,320 | 4/1983 | Nguyen | 604/368 |
| 4,559,050 | 12/1985 | Iskra | 604/368 |
| 4,610,678 | 9/1986 | Weisman | 604/368 |
| 4,701,237 | 10/1987 | Lassen | 156/252 |

FOREIGN PATENT DOCUMENTS 2319309 11/1974 Fed. Rep. of Germany .
433430 5/1984 Sweden .

Primary Examiner—Caleb Weston
Attorney, Agent, or Firm—Shlesinger & Myers

[57] ABSTRACT

A method for producing an absorption body, notably for use in cases of female incontinence which include forming a core by dry depositing a layer of hot meltable thermoplastic fibers and a highly absorbing pulverulent material, e.g. a cross-linked polymer prepared from a methacrylic monomer, on a porous sheet, subjecting the layer to heat treatment to form a stable three-dimensional fiber network and cutting or milling several preferably rectilinear, deep channels in the core surface.

14 Claims, 2 Drawing Sheets

METHOD FOR PRODUCING AN ABSORPTION BODY, NOTABLY FOR USE IN CASES OF URINARY INCONTINENCE IN WOMEN

This is a continuation, of application Ser. No. 855,640, filed Apr. 16, 1986, now abandoned.

FIELD OF THE INVENTION

The present invention relates to a method for producing an absorption body notably meant for use in cases of urinary incontinence in women. In principle the method provides a body which is also suitable for use as a diaper, as a dressing material for highly suppurating wounds and as an absorbing material for purulent matter and other liquids flowing from surgical operations. The method according to the invention provides an absorption body containing a channeled core formed by cutting or milling of a highly absorbent material, which may also find industrial use, as for example, in chemical laboratories.

BACKGROUND OF THE INVENTION

Many embodiments of diapers, sanitary napkins and catamenial tampons and similar absorption bodies are known. However, no known construction is particularly suitable for female urinary incontinence, which poses certain quite special demands. The absorption body must be flat, have a modest thickness in the dry condition and have a suitable width. It must be fairly uniform in its entire length and width, first so as to not require the exertion of a high degree of precision at its application and secondly so as to cause no harm if displaced while being worn by the user, such displacement being almost inevitable.

A particularly important requirement is that the absorption body is able to absorb very rapidly a significant amount of urine. In cases of female urinary incontinence it frequently happens that in a vigorous flow (15–25 ml/sec.) urine flows out for, e.g., ½ to several seconds. These amounts of urine should be subject to immediate absorption and avoid overflow. A total absorption capacity in the absorption body of for instance 70 ml in a number of cases may be considered sufficient, but for some disorders it must be greater. An absorption body for the main purpose stated thus must have properties different from those of sanitary napkins which are to absorb a fluid flowing more constantly and slowly and having a much higher viscosity than urine.

It is known to manufacture absorption bodies with a receiving chamber from which urine may be distributed into the core of the absorption body. This has been found, however, to involve the drawback that the urine may have difficulties in being distributed into the entire core because the parts thereof bordering on the receiving chamber are rapidly saturated with a corresponding reduction of through-flow. In these cases, conventional sanitary napkins have a tendency to press out the urine when compressed from urine absorption.

It will be understood that an absorption body for the present particular purpose must have a series of properties. One of them is that the above-mentioned receiving chamber is replaced by a number of channels—preferably rectilinear and parallel—in the core body responsible for the absorption of the urine.

From DK patent specification No. 122,636 there is known a diaper of a highly absorbent material, preferably dry-fibered cellulose, having several depressions (which may be rectilinear and largely parallel). The depressions have been made by compression. The considerable disadvantage in such an absorption body arises because the compression will slow down somewhat the rate of the absorption of fluid and thereby render the diaper unsuitable for the absorption of such vigorous flow of urine generally experienced in the case of incontinence.

From the German published specification No. 2 319 309, which is mainly concerned with the kind of absorbing material (CMC-derivatives), it is known to provide a core with longitudinal, parallel depressions. It appears that the material is formed by embossing, i.e. compression, and thereby have the above-mentioned drawback in relation to an absorption body with the purpose here aimed at.

From U.S. Pat. No. 3,343,543, Glassman, there is known a sanitary napkin provided with troughs for the absorption of liquid. These troughs normally have been formed by compression with similar drawbacks described above. However, it is also stated that the napkins may be formed by cutting although there is no explanation how or for what purpose. Glassman also represents that one or more layers of wrinkled or grooved paper may be present in the body of the napkin between its upper and lower faces to retard the flow of fluid to the bottom region thereof. The purpose of these layers is to ensure total absorption by the upper region of the napkin before a material quantity of the fluid reaches and is absorbed by the lower portion. As such, with this absorbing object one does not attempt to obtain the fastest possible rate of the absorption of fluid. Presumably this is connected with the fluid characteristics, i.e. higher viscosity of the material to be absorbed and perhaps also with the fact that it comes in a relatively slow flow.

From U.S. Pat. No. 3,411,504, there is known a sanitary napkin in which the surface facing the source of fluid is provided with a ridge situated between two grooves, the ridge being adapted to fit in between labiae majorae in order to ensure against leakage. The grooves are preferably formed by compression, that method being stated to increase the absorption capacity. Such an absorbing object is not suitable for the purpose of the present invention, i.e. because there are precisely only two grooves and the object therefore cannot absorb uniformly and evenly over its entire surface.

BRIEF DESCRIPTION OF THE INVENTION

It is the object of the invention to provide a method for producing an absorption body that remedies the described drawback in the prior art and represents a combination of properties such that it is particularly suitable for use in cases of female urinary incontinence.

This is obtained by the method according to the invention which incorporates the following combination of steps: (a) dry-depositing on a thin, coherent, porous sheet material a core material mixture of (i) a fibrous material substantially consisting of fibers of which at least a part is selected from the class consisting of hot-meltable thermoplastic material, and (ii) a highly absorbent, pulverulent material (superabsorber), (b) subjecting the sheet material with the deposited layer of the mixture to a heat treatment at a temperature just sufficient to soften the thermoplastic surface of the said fibers and within the range of 90° to 175° C. so as to cause the fibers of which at least the surface is thermoplastic to adhere to each other at the spots of contact and to the sheet material, thereby forming a three-dimensional network in which the particles of the pulverulent material are evenly distributed, and (c) cutting or milling the body to removing a substantial proportion of core material so as to form a plurality of channels in the surface of the thus-formed pad opposite the sheet material, the channels having a depth of 65-95% of the thickness of the pad, a width of each at least 4 mm and leaving at least 4 mm of core material between each two neighboring channels.

The principle of dry-depositing materials such as the core in question is well known. The material from which the materials are to be prepared is deposited from an air-current on a suitable (optionally removable) support. Some degree of stratification is thereby achieved so that the material becomes somewhat anisotropic, yet not more so than it is justifiable to maintain a uniform structure through the thickness. In the finished product this stratification maintains such uniformity by absorption of liquid where the pad only expands in the height dimension and the pad's width and length dimensions remain substantially unaffected. Such shape stability of the absorption body not only is important for the ii s comfort when worn but is also important for maintaining the open cross-section of the channels following first absorption of fluid thereby permitting subsequent absorption of newly introduced liquid with approximately the same efficiency.

In preparation the portion of the fibrous material for the structure-giving component, in practice, will be present as staple fibers or comparatively short lengths of filaments. This part of the content of the pad according to the invention preferably consists of fibers of a thermoplastic material; polyethylene fibers have proved particularly suitable but even polypropylene fibers are suitable. In principle, any thermoplastic fibers may be used which can be hot-melted within a reasonable temperature range, e.g. 90°-175° C. Additionally, the fibrous material may be composed from natural fibers or other non-thermoplastic fibers coated with a thermoplastic material.

A thermoplastic surface is important. Following deposit of the fibers on the support, the fibers are heated to a temperature sufficient to soften the surfaces of the fibers so that the fibers will adhere to each other at the spots of contact. This results in the formation of a three-dimensional fiber network. Additionally, the heat-treated fibers, now forming a thin, coherent layer, contribute to the stiffening of the overall structure.

The three dimensional fiber network serves to retain the other components of the pad, the most important being the highly absorbent material which is sometimes designated (and may be commercially available) with the name "superabsorber". Superabsorbers may be either pulverulent or fibrous materials. The three dimensional fiber network is essential in retaining the superabsorber when in the form of a pulverulent (powder).

Superabsorbers are commercially available and are based, for example, on cellulose or starch derivatives and on cross-linked polymers of acrylic or methacrylic monomers. One kind of such a material that has proven very suitable for the present purpose is that sold under the name of "Favor" (a registered trademark) and is supplied by Chemische Fabrik Stockhausen, Krefeld, BRD. This particular material can absorb up to many hundred times its own weight of distilled water. The absorbing power of various kinds of superabsorbers for urine ranges from 10-80 times the superabsorber weight. Superabsorbers exist with varying rates of absorption although generally rapid. Selecting absorption rates affords the possibility of obtaining an optimal effect. Generally, the amount of superabsorber is typically 1.5-5 g per absorption body. The materials are insoluble but highly swellable in water. Due to the foregoing characteristics, superabsorbers have been adopted for use in connection with incontinence.

If desired, the thermoplastic fibers may, according to the invention, be supplemented with cellulose fluff which is an inexpensive material having a measurable absorbent capacity although far less than cellulose or acryl based superabsorbers as described above.

It is here mentioned that expediently the pad has a thickness of 2-7 mm, e.g. 3-6 mm and preferably about 5 mm.

Moving now to another consideration of the invention, it is the requirement that the channels have a depth of 65-95% of the thickness of the pad. In so forming the channels to such a depth, the absorbing surface, which now includes not only the face of the pad but also the walls of the channels, is enhanced considerably. Accordingly, when urine flows from the uretha, the major portion thereof will at once flow into the channels where the channels prevent escape of a portion of the urine from the absorption body to wet the legs or underwear of the wearer. Moreover, as noted above, the channels serve to provide a large surface area so that the urine will immediately be absorbed from the channel walls and bottoms, where the channels are milled or cut, as described, as the absorption body incorporates a superabsorber.

The channels must be formed by a working of cutting or milling, and only following heat treatment of the pad necessary to provide the stable structure, not by compression or embossing. This has several advantages. It avoids embossing or compression of the pad to form the channels which will reduce the rate of absorption of the urine. Furthermore, an economic advantage is achieved because the material cut away, notably the superabsorber, generally the most expensive part of the absorption body, then may be recycled and used in a new pad.

It will be understood that a rather considerable amount of material is cut away or milled away from the pad after the dry-depositing. In practice, the amount of material is normally about 30%, in some cases perhaps as low as about 25%. The thin, coherent layer of material, the core, even after the removal of such large amounts of material, does have sufficient strength and rigidity to exhibit the appearance of a flat, flexible pad which resists deformation of the channels.

The channels must have a width of at least 4 mm in order to facilitate distribution and immediate absorption of the urine stream by the absorbing channel walls. There must be at least 4 mm between two neighboring channels so as to ensure a sufficient amount of material between the channels, in addition to the channel bottom surface, for absorption. Preferably, the channels are about 5 mm wide and have an intermediary ridge having a width of about 7 mm.

DESCRIPTION OF THE DRAWING

In the following the invention will be described more fully with reference to the drawing in which.

DETAILED DESCRIPTION OF THE ILLUSTRATED EMBODIMENT

Figure 1:
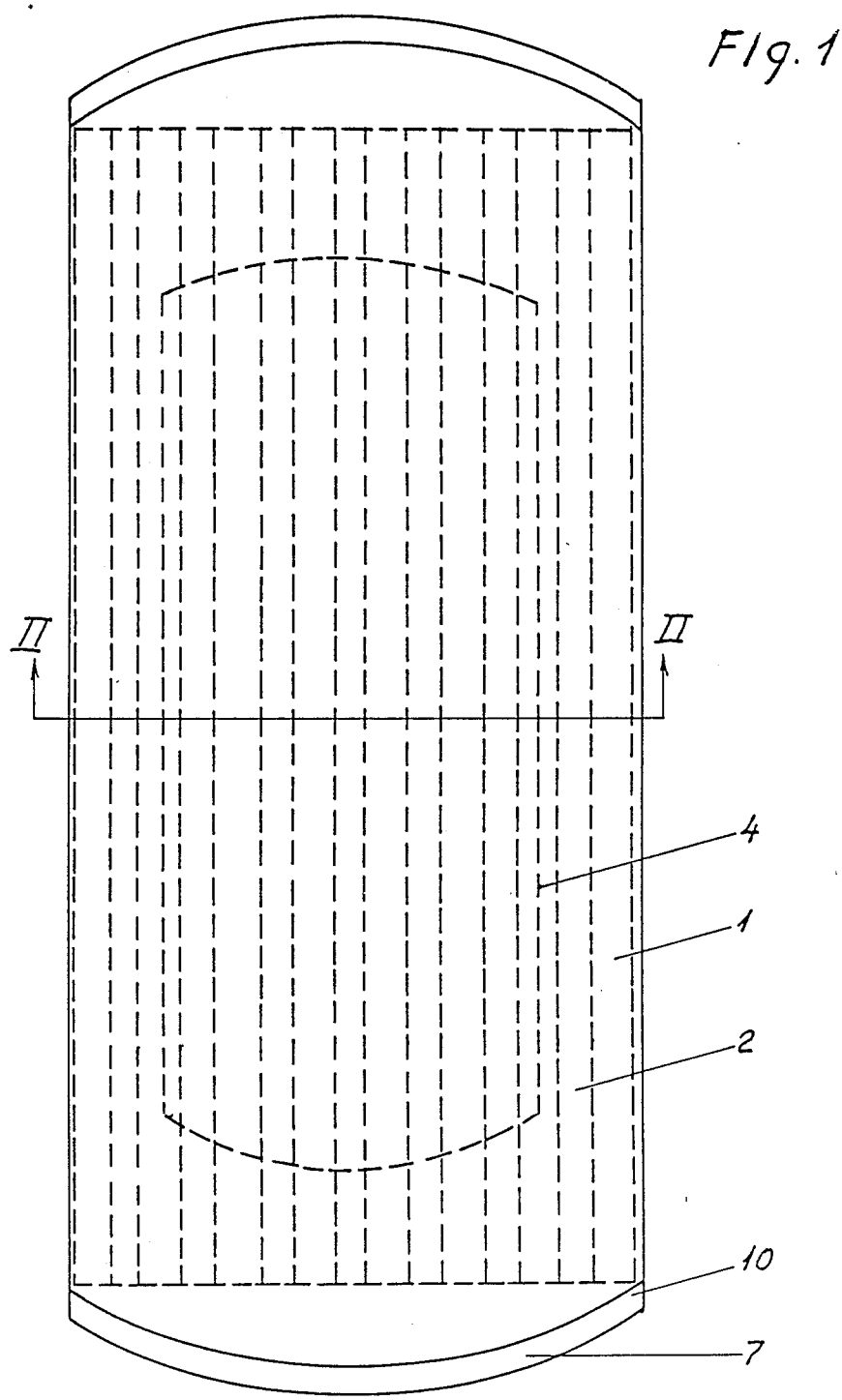
FIG. 1 shows a plan view of an absorption body according to the invention, the core being indicated by dashed lines.

In the drawing the absorption body according to the invention is shown in a preferred embodiment particularly well suited for use in cases of female urinary incontinence. Inside the body there is a core 1 on which there has been placed various fluid distributing and absorbing layers, and outermost the absorption body is surrounded by a casing 7.

The core 1 has been prepared by dry-deposition in a continuous operation, and seen from above it has a rectangular shape as appears from FIG. 1. The core may have a width of about 85 mm and a thickness of about 5 mm. The thickness may vary according to the desired absorption capacity and flexibility of the absorption body. The thickness will be between 2 and 12 mm, generally between 3 and 6 mm and preferably 5 mm. The material normally includes a mixture of cellulose fluff, a filler having a high capacity for absorbing fluids. However, the presence of cellulose fluff is optional. The presence of the below-described thermoplastic fibers is mandatory. For example, material composed of about 38% cellulose fluff by weight, about 16% by weight of thermoplastic fibers and about 46% by weight of a superabsorber is satisfactory for this invention.

The superabsorber may be either pulverulent or fibrous and based on cellulose or starch derivatives, or cross-linked polymers of acrylic or methacrylic monomers. One such suitable material is sold under the mark "Favor" (registered trademark) and is supplied by Chemische Fabrik Stockhausen, Krefeld, BRD.

For the thermoplastic fibers, polyethylene fibers are particularly suitable. Polypropylene fibers also function well. The fibrous material may even be natural fibers or other non-thermoplastic fibers coated with a thermoplastic material. In principle, any kind of thermoplastic fiber may be employed so long as the fibers can be hot-melted within a reasonable temperature range, e.g. 90°–200° C. The upper limit of the hot-melt temperature range is normally established by the temperature sensitivity of the superabsorber. Often, superabsorbers are incapable of surviving temperatures above 160°.

The superabsorbers containing core is produced by the dry-deposition of the superabsorber. The superabsorber fibers are suspended in an air current and deposited on a selected length of a thin, coherent, porous material, e.g. paper. The air is extracted via the pores of the material. Preferably, the resulting product has a thickness of 5 mm and a density of about 550 g/m². By this process, the fibers primarily are oriented in planes extending approximately parallel to the upper and lower faces of the core. The functional result is that the swelling caused by absorption of fluid into the core takes place substantially in the direction of the thickness of the core. Hence, the risk that the fluid will be pressed out by a local compression of the absorbent body is minimized.

Core 1 is provided with elongated, straight channels or grooves 2 parallel to its upper face. These channels or grooves 2 are formed after the absorbent body has been subjected to a heat treatment, (e.g. 90°–200° C. depending on the thermoplastic material) required to fuse the thermoplastic fibers. Such fusion occurs at the fiber intersections and produces a three-dimensional lattice having a considerable shape stability. As noted above, normally the melting point characteristics of the superabsorber defines the upper limit of the temperature.

The remaining components of the core are evenly distributed within this lattice structure. The resulting structure, the combination of core 1 and paper layer 3, has a sufficient strength to allow the channels 2 to be formed by cutting or milling. The channels must have a width of at least 4 mm and there must be at least 4 mm between two neighbor channels. Ordinarily, the channels are made at a width of 5 mm and with 7 mm width of the intermediary parts and the channel depth is 65–95% of the thickness of core 1. The channels constitute distributing paths for fluid in the absorbent body and considerably increase the surface through which the fluid can penetrate into the body. Also, the channels maximize absorbent surface area by providing side walls and a bottom surface composed of a fiber network oriented in planes approximately parallel to the upper and lower faces of the pad. The superabsorber is selected to exhibit a moderate rate of absorption where the fluid (urine) will have time to spread over a substantial portion of the core, so as to efficiently utilize the absorption capacity of the entire core comparatively uniformly. Furthermore, the absorption body is better capable to receive a number of brief flows of urine at discrete time intervals. The material cut or milled away during the preparation can be re-used in the dry deposition process for which reason the forming of the channels does not cause waste of the superabsorber. This concept provides greater economic efficiencies as the superabsorber comprises a substantial part of the costs of material for the preparation of the absorption body.

By the dry-deposition process the core of the absorption body as mentioned is provided with a paper layer 3. Paper layer 3 minimizes the tendency of the absorbent body to be squeezed together from the sides and contributes to maintain open channels. This paper layer contributes at distributing the fluid and in itself is even able to absorb part of the fluid. However, the most important function of the paper is to assist in providing structural integrity by preserving the core during and after the milling of the channels 2.

Disposed under paper 3 is a highly absorbing layer 4 of material. Layer 4 may be prepared in a similar manner to core 1 by dry-deposition of a mixture consisting of about 35% by weight of fluff, about 15% by weight of thermoplastic fibers and about 50% by weight of superabsorber. It is preferred that layer 4 have a thickness of 1.5 mm and a weight of about 350 g/m², in contradistinction to core 1 proper (about 550 g/m²). The layer 4 has the purpose of increasing the absorption capacity and it may have various shapes such as hour-glass shape or the like. In this manner it is possible to ensure optimal absorbent capacity at the ends of the absorption body. If a particularly high absorption capacity is not needed, however, the highly absorbing layer 4 may be dispensed with entirely or partly.

Where the pad is contemplated for a use requiring a particularly high absorption capacity, the absorption body may be rendered both thicker and bigger. It may be produced to have such enhanced size that it extends beyond the contour of the ends of the core. Therefore, the middle of the body is somewhat narrower than core 1. To reduce costs, layer 4 may be replaced by or supplemented with a diaper of cellulose fluff with the major parts of the diaper's volume being disposed at the ends of core 1. By such provision, the total absorption capacity may be increased to 200-500 ml which corresponds to the entire content of a full urinary bladder. The diaper embodiment contemplates maximizing use of distributing properties and the large absorbing capability of the core to absorb the entire volume of urine.

Turning to convenience, since substantially only the distributing core of the absorption body is present in the area between the legs of the wearer, this form of a diaper provides considerably more comfort than traditional diapers. At the normal absorption capacities (about 70 ml) there is special importance attached to user comfort and confidence. Furthermore, compact size coupled with substantial absorption capacity minimizes user concern when dressing.

Figure 2:
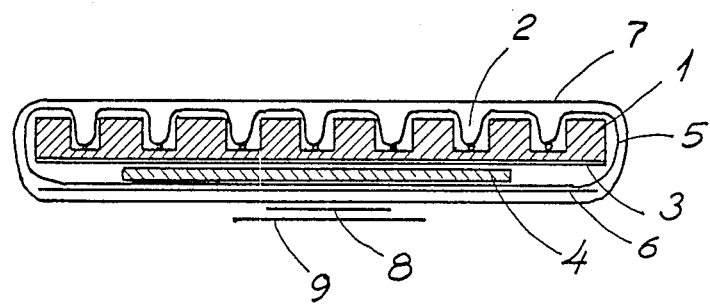
FIG. 2 is a section of the absorption body along line II—II in FIG. 1.

Turning again to FIG. 2, core 1 and the optional layer 4 may be wrapped in one or more layers 5 of paper where one or more layers 5 may have been positioned at and secured to the bottom of the channels 2. Securing layers 5 may be achieved with the aid of glue. To press layers 5 into channels 2 may be accomplished with the aid of rollers or the like. The purpose of this or these layer(s) of paper is, first, to contribute to uniform distribution of the fluid throughout the surface of the body, and, secondly, to keep the pulverulent superabsorber material within the core material. Hence, the possibility of fluid being pressed through the core without being absorbed is minimized. Preferably, the paper comprising layers 5 is only fixed at the bottoms of the channels so as not to interfere with expansion of the core. Furthermore, such positioning promotes user comfort when the absorption body is worn against the skin.

Referring now to the under side of the absorption body, it is provided with a liquid-tight layer 6 which prevents seepage of fluid.

The entire absorbent body described above, namely; core 1 having channels 2 on paper support 3 overlying optimal absorbent strip 4 all surrounded by paper layer 5, is enveloped in a non-woven material layer 7 which is skin compatible and which encloses the absorption body in a closed envelope.

The final shape of absorbent bodies described above have lengths of about 180 mm, as illustrated in FIG. 1 and may be straight or curved. In the case where the body is curved, the cut-off portions of core 1 and absorbing layer 4 may be re-used. Ends 10 are closed by glueing, hot melting or the like. The above-described absorption body, if needed, may be provided with a conventional adhesive layer 8 at the lower face whereby the absorption body may be maintained as an ordinary napkin in the pants of the user. For additional convenience, the adhesive layer 8 may be covered with a releasable silicone coated cover 9. Cover 9 is removed just prior to use of the absorption body Although the absorption body according to the invention mainly is described as a protection in cases of incontinence, for which purpose its ability to very rapidly absorb significant amounts of fluid released in one or more comparatively short but comparatively strong flows is indispensable, it is within the framework of the invention to use the absorption body for absorbing other human secretions. Of course, the shape and the size of the absorbent body may be varied according to need. As examples of such uses may be mentioned diapers, sanitary napkins and wound dressings, but even purely technical uses may come into consideration.

I claim:

1. A method for producing an absorption body for use in cases of female urinary incontinence and containing a core in the form of one flat absorbent pad provided with channels, comprising the steps of:

(a) subjecting the sheet material with the deposited layer of the mixture to a heat treatment at a temperature just sufficient to soften the thermoplastic surface of the said fibers and within the range of 90° to 175° C. so as to cause the fibers of which at lest the surface is thermoplastic to adhere to each other at the spots of contact and to the sheet material, thereby forming a three-dimensional network in which the particles of the pulverulent material are evenly distributed, and (c) cutting or milling the body to remove a substantial proportion of core material so as to form a plurality of channels in the surface of the thus-formed pad opposite the sheet material, the channels having a depth of 65-95% of the thickness of the pad, a width of each at least 4 mm and leaving at least 4 mm of core material between each two neighboring channels.

2. A method as claimed in claim, comprising the further step of wrapping the core formed into a thin, liquid permeable layer of material to form a casing, leading this casing into the channels to their bottoms.

3. A method as claimed in claim 2, wherein the core material mixture consists of 40-50% by weight of a pulverulent, cross-linked acrylic polymer, 10-14% by weight of thermoplastic fibers and 30-50% by weight of cellulose fluff.

4. A method as claimed in claim 2, comprising the further step of placing a flat, highly absorbent layer of fibers and pulverulent cross-linked polymer between the core and the casing, on the side of the fibrous sheet turned away from the channels, said layer having a smaller thickness than the core.

5. A method as claimed in claim 1, further including the step of incorporating fluff into the fibrous material.

6. A method as claimed in claim 5, wherein the fibrous material defined in claim 1 (a) (i) consists of a mixture of thermoplastic fibers and cellulose fluff in a weight ratio of about 1:2.5.

7. A method as claimed in claim 1, wherein the amount of core material removed by the cutting or milling operation is at least 25% of the entire volume of core material.

8. A method as claimed in claim 1, wherein the amount of core material removed is 30% of the volume of core material.

9. In a method for producing an absorption body for use in cases of female urinary incontinence and containing a core in the form of one flat absorbent pad provided with channels, comprising the steps of (a) dry-depositing on a thin, coherent, porous sheet material a core material mixture of (i) a fibrous material substantially consisting of fibers of which at least a part is selected from the class consisting of hot-meltable thermoplastic material and fibers of another material but provided with a hot-meltable thermoplastic surface coating, and (ii) a highly absorbent, pulverulent material, (b) subjecting the sheet material with the deposited layer of the mixture of fibrous material and pulverulent material to heat treatment at a temperature just sufficient to soften the thermoplastic surface of the said fibers and within the range of 90° to 175° C. so as to cause the fibers of which at least the surface is thermoplastic to adhere to each other at the spots of contact and to the sheet material, thereby forming a pad comprising a three-dimensional network in which the particles of the pulverulent material are evenly distributed and (c) forming a plurality of longitudinal channels in the surface of the thus-formed pad opposite the sheet material, the channels having a depth of 65-95% of the thickness of the pad, a width of each at least 4 mm and leaving at least 4 mm of core material between each two neighboring channels, the improvement which comprises forming the longitudinal channels by cutting and recovering the cut surface portions.

10. A method as claimed in claim 9, wherein the amount of core material removed by the cutting is at least 25% of the entire volume of core material.

11. A method as claimed in claim 9, wherein the amount of core material removed is 30% of the volume of core material.

12. In a method for producing an absorption body for use in cases of female urinary incontinence and containing a core in the form of one flat absorbent pad provided with channels, comprising the steps of (a) dry-depositing on a thin, coherent, porous sheet material a core material mixture of (i) a fibrous material substantially consisting of fibers of which at least a part is selected from the class consisting o hot-meltable thermoplastic material an fibers of another material but provided with a hot-meltable thermoplastic surface coating, and (ii) a highly absorbent, pulverulent material, (b) subjecting the sheet material with the deposited layer of the mixture of fibrous material and pulverulent material to a heat treatment at a temperature just sufficient to soften the thermoplastic surface of the said fibers and within the range of 90° to 175° C. so as to cause the fibers of which at least the surface is thermoplastic to adhere to each other at the spots of contact and to the sheet material, thereby forming a pad comprising a three-dimensional network in which the particles of the pulverulent material are evenly distributed, and (c) forming a plurality of longitudinal channels in the surface of the thus-formed pad opposite the sheet material, the channels having a depth of 65-95% of the thickness of the pad, a width of each at least 4 mm and leaving at least 4 mm of core material between each two neighboring channels, the improvement which comprises forming the longitudinal channels by cut milling and recovering the cut surface portions.

13. A method as claimed in claim 12, wherein the amount of core material removed by the milling is at least 25% of the entire volume of core material.

14. A method as claimed in claim 12, wherein the amount of core material removed is 30% of the volume of core material.

* * * * *